US00PP23268P2

(12) United States Plant Patent
Korlipara

(10) Patent No.: US PP23,268 P2
(45) Date of Patent: Dec. 18, 2012

(54) ***CAMPANULA* PLANT NAMED 'SUMMERTIME JAZZ'**

(50) Latin Name: ***Campanula* hybrid (*C. punctata* 'Bowl of Cherries'×*C. glomerata* 'Superba')**
Varietal Denomination: Summertime Jazz

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 13/200,460

(22) Filed: Sep. 22, 2011

(51) Int. Cl.
*A01H 5/00* (2006.01)
(52) U.S. Cl. ..... Plt./414
(58) Field of Classification Search ..... Plt./414
See application file for complete search history.

*Primary Examiner* — Annette Para
(74) *Attorney, Agent, or Firm* — Klarquist Sparkman, LLP

(57) ABSTRACT

A new and distinct *Campanula* plant characterized by large bells of deep violet blue flowers, short flower stalks, multiple inflorescences, no seed set, and long bloom time (June through September with deadheading in Canby, Oreg.).

1 Drawing Sheet

Botanical classification: *Campanula* hybrid (*C. punctata* 'Bowl of Cherries'×*C. glomerata* 'Superba').

Variety denomination: 'Summertime Jazz'.

BACKGROUND

The present invention relates to a new and distinct *Campanula* plant that is given the cultivar name of 'Summertime Jazz'. *Campanula* is in the family Campanulaceae. *Campanula* 'Summertime Jazz' originated from a planned cross for a *Campanula* 'Sarastro' type with a shorter habit. It is a cross between *Campanula punctata* 'Bowl of Cherries' (U.S. Plant Pat. No. 13,194), as the seed parent, and *Campanula glomerata* 'Superba' (an unpatented plant), as the pollen parent. The offspring from the cross were planted out and this selection was made for its fine characteristics.

Compared to the seed parent, *Campanula punctata* 'Bowl of Cherries', the new cultivar is taller and has blue rather than pink flowers.

Compared to the pollen parent, *Campanula glomerata* 'Superba', the flowers are larger, less congested, and less blue in flower color.

Compared to *Campanula* 'Summertime Blues', U.S. Plant Pat. No. 19,261, the new cultivar is shorter, with narrower inflorescences, and darker violet blue flowers.

This new and unique *Campanula* hybrid is distinguished by:

1. large bells of deep violet blue flowers,
2. short flower stalks,
3. multiple inflorescences,
4. no seed set,
5. and long bloom time with deadheading (June through September in Canby, Oreg.).

This new cultivar has been reproduced only by asexual propagation (tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a 2 year old *Campanula* 'Summertime Jazz' growing in the ground in the garden in full sun in July in Canby, Oreg.

DETAILED PLANT DESCRIPTION

The following is a detailed description of the new *Campanula* based on observations of two year old specimens grown in the garden outside in part sun under typical weathers in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart, 5$^{th}$ edition.

Plant:
- *Form.*—Rosette-forming herbaceous perennial.
- *Hardiness.*—USDA Zone 4-9.
- *Size.*—45 cm tall from the ground to the top of the inflorescence and 46 cm wide.
- *Habit.*—Upright, clumping, not many basal leaves.
- *Crown number.*—10 to 15 rosettes.
- *Vigor.*—Excellent.

Stem/peduncle:
- *Type.*—Flowering.
- *Size.*—15 cm to first flower.
- *Surface.*—Pubescent.
- *Internode length.*—1 to 3.5 cm.
- *Color.*—Greyed Purple 187A.

Leaf:
- *Type.*—Simple.
- *Arrangement.*—Basal and alternate up the stem.
- *Shape.*—Basal leaves ovate, stem leaves lanceolate to ovate lanceolate.
- *Venation.*—Main central vein with secondary veins palmate.
- *Margins.*—Double serrate, undulate.
- *Apex.*—Acute.

*Base*.—Basal leaves cordate, stem leaves attenuate at the bottom of the stem to clasping at the top.

*Surface texture*.—Pubescent on both sides.

*Blade size*.—Basal leaves grow to 4.5 cm long and 2.6 cm wide; stem leaves are variable in size, lower leaves growing to 8 cm long and 2.2 cm wide.

*Petiole description*.—Basal leaves have petioles 3 cm long and 1 mm wide, pubescent, Green 137A tinted Greyed Purple 187B.

*Leaf color*.—Topside Green 137A with margins tinted Greyed Purple 187A, bottom side Yellow Green 147B tinted Greyed Purple 187A towards the outside edge.

Inflorescence:

*Type*.—Few flowered terminal panicle.

*Size*.—About 27 cm long and 9 cm wide.

*Number of flowers*.—10 to 15 flowers per panicle.

*Pedicel*.—0 to 8 mm long and 1 mm wide, pubescent, Greyed Purple 187A.

*Bloom period*.—June through August in Canby, Oreg.

Flower bud:

*Size*.—8 cm wide and 42 cm long.

*Shape*.—Tubular, elongate, pleated.

*Surface*.—Glabrous.

*Color*.—Violet Blue 90A.

Flower:

*Type*.—Actinomorphic.

*Shape*.—Campanulate, cylindrical.

*Size*.—5 cm long and 3.3 cm wide.

*Corolla*.—46 mm long; with tube 32 mm long and 20 mm wide, 5 lobes, each 12 mm long and 10 mm wide, reflexed, shape triangular, with 1.5 mm long and 1.5 mm wide triangular appendage at the base on each side projecting backward, margins entire, tip acute, surface inside villous, outside glabrous, outside color Violet Blue 90A, inside color between Violet Blue N87A and N88A.

*Calyx*.—18 mm wide and 2 cm deep, campanulate with 5 lobes, tube 5 mm long and 6 mm wide at lobe junction, lobes are 15 mm long, 4 mm wide at the base, between each lobe is a strongly reflexed appendage (5 mm wide and 5 mm long, tips acute), lobes with tips acuminate, lobes and appendages with margins entire and pubescent, top and bottom sides glabrous and Yellow Green 144B tinted Greyed Purple 187A.

*Stamen*.—5, filaments 3 mm long and less than 1 mm wide, White NN155C, anthers are 9 mm long and 1 mm wide, White NN155D.

*Pistil*.—Ovary is 4 mm deep and 7 mm wide, pubescent, White NN155C, style 2.2 cm long and less than 2 mm wide, 3-branched stigma, each reflexed branch 4 mm long and 1 mm wide, White NN155C.

*Fragrance*.—None.

*Lastingness*.—Each flower lasts for about 5 days on the plant.

Fruit and seed: None.

Diseases and pests: No diseases found of this new variety. No known disease resistance. Many *Campanula* sp. are susceptible to snails, slugs, and aphids.

I claim:

1. A new and distinct *Campanula* plant as herein illustrated and described.

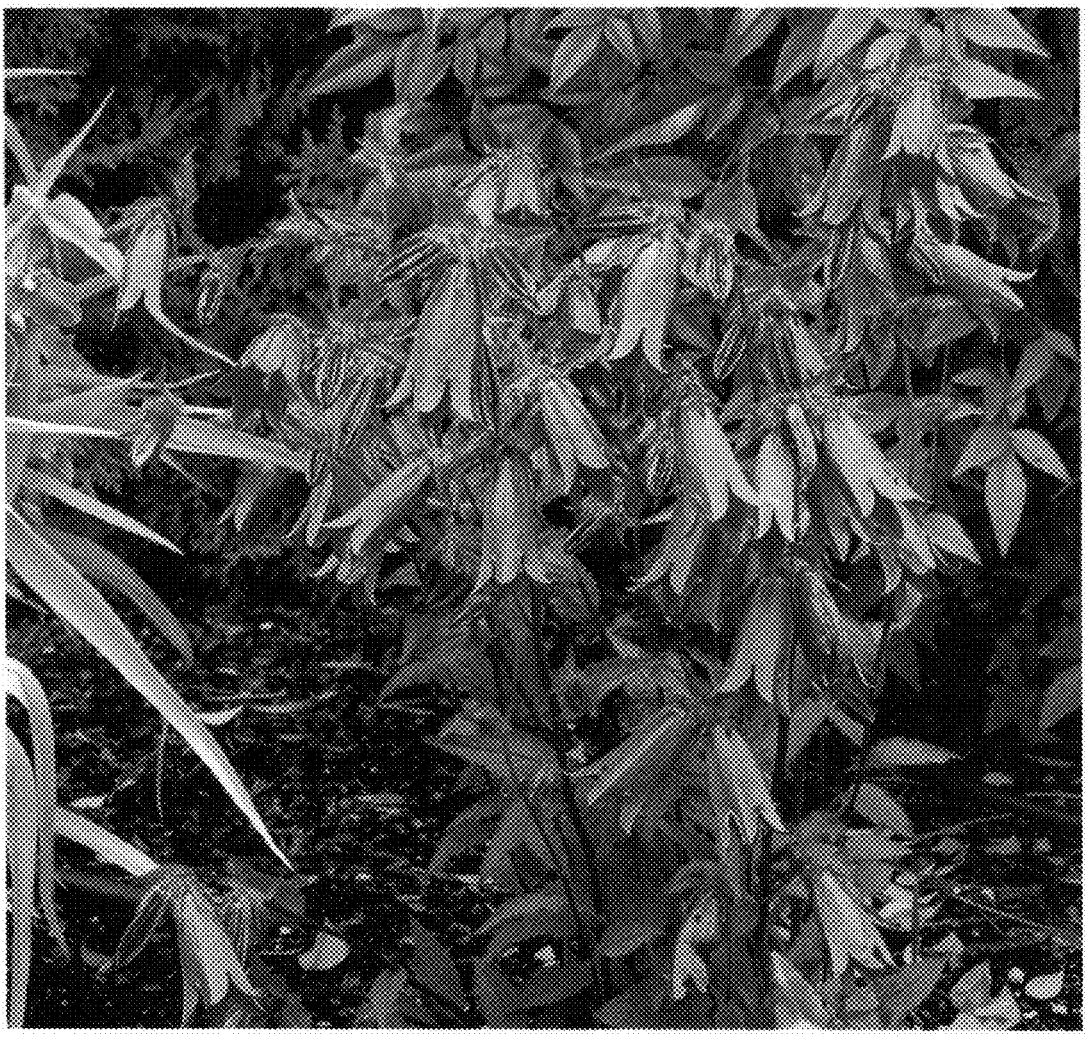

* * * * *